(12) United States Patent
Whelan et al.

(10) Patent No.: US 7,178,416 B2
(45) Date of Patent: Feb. 20, 2007

(54) RADIO FREQUENCY IDENTIFICATION (RFID) TEST INFORMATION CONTROL AND TRACKING SYSTEM

(75) Inventors: James P. Whelan, Lake Forest, IL (US); C. Michael Hanbury, Huntington Beach, CA (US)

(73) Assignee: Alexeter Technologies, LLC., Wheeling, IL (US)

( * ) Notice: Subject to any disclaimer, the term of this patent is extended or adjusted under 35 U.S.C. 154(b) by 114 days.

(21) Appl. No.: 10/887,433

(22) Filed: Jul. 8, 2004

(65) Prior Publication Data

US 2005/0009122 A1    Jan. 13, 2005

Related U.S. Application Data

(60) Provisional application No. 60/485,557, filed on Jul. 8, 2003.

(51) Int. Cl.
*G01N 21/77* (2006.01)
*G01N 33/48* (2006.01)

(52) U.S. Cl. ............... 73/864.91; 73/61.48; 73/61.71; 73/64.56; 73/864.83

(58) Field of Classification Search ......... 73/61.48, 73/61.71, 64.56, 864.81–864.83, 864.91, 73/431, 865.8, 866
See application file for complete search history.

(56) References Cited

U.S. PATENT DOCUMENTS 4,226,536 A * 10/1980 Dreyfus et al. ............ 356/602
6,738,903 B1 * 5/2004 Haines .................... 713/168
6,802,659 B2 * 10/2004 Cremon et al. ............ 400/76
2002/0031446 A1 * 3/2002 Friedlander et al. ....... 422/68.1

OTHER PUBLICATIONS

"The Guardian BTA Test Strip Reader", Alexeter Technologies, LLC., Jan. 1, 1999, available on the Internet at <http://web.archive.org>.*
"Technical Bulletin #3", Alexeter Technologies, LLC., May 28, 2002.*
"Technical Bulletin #1", Alexeter Technologies, LLC., Feb. 20, 2002.*
"Evidence Tables", HSTAT, available on the Internet at <http://www.ncbi.nlm.nih.gov>, see pp. 11 and 12.*
"Anthrax Bio Threat Alert Test Strip", Tetracore, 238 May 2002.*
"Ricin Bio Threat Alert Test Strip", Tetracore, 238 May 2002.*
"Bo Tox Bio Threat Alert Test Strip", Tetracore, 238 May 2002.*

(Continued)

*Primary Examiner*—Hezron Williams
*Assistant Examiner*—David A. Rogers
(74) *Attorney, Agent, or Firm*—Welsh & Katz, Ltd.

(57) ABSTRACT

In one embodiment, a system for analytical testing comprises a test cartridge for use in conducting an analytical test including a test medium and an RFID device. An encoding device is provided adapted to preprogram the RFID with information relating to the test. An analytical detection device including a RFID transceiver adapted to transfer data to and from the RFID device is coupled to test detection instrumentation adapted to analyze the test medium in response to the information relating to the test.

14 Claims, 3 Drawing Sheets

OTHER PUBLICATIONS

"SEB Bio Threat Alert Test Strip", Tetracore, 238 May 2002.*
"Plague Bio Threat Alert Test Strip", Tetracore, 237 May 2002.*
"Tularemia Bio Threat Alert Test Strip", Tetracore, 238 May 2002.*
"Testing Times", Economist.com, Oct. 20, 2001.*
The Guardian BTA ™ System Alexeter Technologies LLC.
The Guardian BTA ™ System (Bio Threat Alert) Alexeter Technologies LLC.
*Product Brief* Guardian BTA ™ (Bio Threat Alert) System Alexeter Technologies LLC.
The Guardian Bio Threat Alert System Alexeter Technologies LLC.
Guardian Bio Threat™ Alert System *Description and Specifications* Alexeter Technologies LLC.
The Guardian Reader™ Manual Instructions Alexeter Technologies LLC R 1000 Mar. 18, 2002.
Alexeter Training Presentation Jan. 19, 2002 Alexeter Technologies LLC.
RFID Workstation Users Guide Ver. 1.0 Feb. 2002 Alexeter Technologies LLC.

* cited by examiner

RADIO FREQUENCY IDENTIFICATION (RFID) TEST INFORMATION CONTROL AND TRACKING SYSTEM

CROSS REFERENCE TO RELATED APPLICATION

This application claims the benefit of provisional application No. 60/485,557 filed Jul. 8, 2003 entitled "Radio Frequency Identification (RFID) Test Information Control And Tracking System.

FIELD OF THE INVENTION

The field of the invention relates generally to analytical test systems and more particularly to an analytical test system using radio frequency identification (RFID).

BACKGROUND

Radio frequency identification chip/antennas combined with radio frequency identification interrogators (collectively, RFID systems) have been utilized in numerous industrial and retail settings for tracking of inventory and capital equipment. Historically, some applications include inventory management in warehouse operations, unit tracking of retail items such as clothing and shoes, uses associated with SMART debit cards, garment tracking in retail and dry cleaning industries, and on livestock to record individual animal location. RFID tracking devices have also been described in healthcare settings for continuous tracking of patient, physician and/or health care worker location within medical centers, asset control for hospital capital equipment, and as a mechanism to track access to controlled areas such as pharmacy.

RFID devices can be programmed to store relatively large amounts of information as compared to traditional bar codes. Unlike traditional bar codes that typically cannot be changed once applied, some RFID devices possess READ/WRITE capability that enables characteristic information about each specific unit of interest to be recorded on the RFID tag during use, either by addition, subtraction or modification of previously encoded information. These modifications can be either written only once or many times depending on the RFID system used.

For most clinical and environmental test systems, existing systems require that information specific to calibration, control, discrimination cut-off values for determination of positive/negative, notification to the user of result in/out of expected range, and other test-specific information be manually input at some defined frequency and/or with each lot number. The approach used by such systems has been for the input of this information to the analytical instrument to be performed by manual intervention including manual keypunch, and/or bar-code, or magnetic-type reader.

Because the relationship of the single-use test device or specimen cup is by nature transitory and such device is either discarded following use or washed or cleansed by some process, prior system did not provide a mechanism for positive tracking of the test device other than by barcode. The bar code technology requires positive line-of-sight and may be adversely affected by the test contents, reagents and/or by physical handling. RFID devices obviate the strict optical direct "line of sight" requirements of bar-code systems.

RFID systems are typically comprised of 1) relatively small (typically 2–625 square millimeters) radio frequency tags that can be permanently or semi-permanently attached to items of interest, 2) a transceiver or interrogator (RFID reader) to read-from and/or write-to the tag, and in some cases, 3) an associated computerized data management system to process discrete information obtained by the interrogator.

In conventional RFID inventory control type systems, specific asset information is encoded onto a series of RFID tags that are attached to the items of interest as required for tracking purposes. On passive tag designs, the items of interest containing the tags are brought near a base station transceiver or interrogator that transmits an excitation radiowave to the powering circuitry on the tag as described. An RFID transceiver or interrogator transmits an amplitude-modulated radio signal followed by a continuous wave radio signal to each tag. The tag modulates the continuous wave signal using modulated back-scattering where the tag's antenna is electrically switched by the tags modulating signal from being an absorber of radiofrequency radiation to a reflector of the energy with the tag's information encoded onto the continuous wave radio signal. Such inductive coupled tags do not have self-contained batteries, have zero maintenance and virtually unlimited lifespan. However, their operating range is limited by the associated antenna and repeater electronics compared to other active tag designs.

In many tracking designs, the tag circuitry communicates the stored information from the tag to the base station that receives and decodes the information. Once encoded, a RFID reader demodulates the incoming continuous wave signal and decodes the information from the tag specific to the associated item. RFID readers are well known in the art and are commercially available for a variety of manufacturers including Motorola and Hitachi. A computer system that interfaces with the reader to direct interrogation of each tag and/or to record pertinent information for each event and for data processing may also be incorporated in an RFID system.

SUMMARY

In one embodiment, a system for analytical testing comprises a test cartridge for use in conducting an analytical test including a test medium and an RFID device programmed with information relating to the test. An analytical detection device including a RFID transceiver adapted to transfer data to and from the RFID device is coupled to test detection instrumentation adapted to analyze the test medium responsive to the information relating to the test.

BRIEF DESCRIPTION OF THE DRAWINGS

The invention, together with the advantages thereof, may be understood by reference to the following description in conjunction with the accompanying figures, which illustrate some embodiments of the invention.

DETAILED DESCRIPTION

Figure 1:
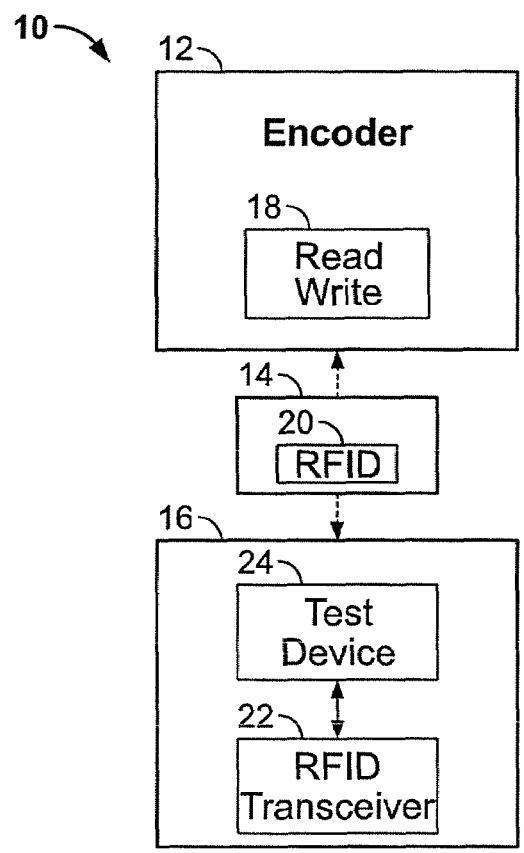
FIG. 1 is a block diagram illustration of one embodiment of an analytic test system with RFID technology.

While the present invention is susceptible of embodiments in various forms, there is shown in the drawings and will hereinafter be described some exemplary and non-limiting embodiments, with the understanding that the present disclosure is to be considered an exemplification of the invention and is not intended to limit the invention to the specific embodiments illustrated. In this disclosure, the use of the disjunctive is intended to include the conjunctive. The use of the definite article or indefinite article is not intended to indicate cardinality. In particular, a reference to "the" object or "a" object is intended to denote also one of a possible plurality of such objects.

This application hereby expressly incorporates by reference the entire disclosure of provisional application No. 60/485,557 filed Jul. 8, 2003.

FIG. 1 is a block diagram illustrating one embodiment of an analytical test system 10 including an encoding device 12, a test device (cartridge) 14 and an analytical detection device 16. The encoder 12 includes a RFID transmitter or transceiver 18 for writing data to a RFID device 20 to program the RFID device 20 with information relating the test cartridge 14 and it associated test. This information may include manufacturing lot number, expiration date, test name, and analytical cut-off to determine positive or negative interpretation of the test results. The encoder may also include other processing and control circuitry (not shown), such as a microcomputer, which may be integral or in a separate enclosure. In one embodiment, the encoder is located at the manufacturing site to enable pre-programming at the time of manufacture and in other embodiments may be located in the field for later programming or reprogramming.

The test cartridge 14 includes the RFID device 20 which may be included inside the cartridge or otherwise attached. The cartridge includes a test medium for performing the desired test, and may be a reusable, disposable, single test, or multi-test cartridge. RFID device 20 typically has associated memory, either integral and separate, for storage of data. This memory typically can be programmed by writing data to the RFID device 20 using an RFID transmitter such as transceiver 18. In some embodiments the RFID device 20 is pre-programmed during the manufacture process, or at some other time prior to use.

The analytical detection device or detector 16 in the illustrated embodiment includes a RFID transceiver 22 (i.e. RFID reader/writer) capable of transferring data to and from the RFID device 20 prior to, concomitantly, subsequently or in combination with performing the analytical measurement and interpretation of the test results. The illustrated detector 16 also includes analytical detection instrumentation (test device) 24, such as is known in the art, coupled to the transceiver 22, to perform the measurement and interpretation. The detector 16 may also include in some embodiments additional processing, control and data storage circuitry (not shown).

The RFID transceivers 18, 22 may include read only or read-write transceivers depending on the application. In read/write systems, the RFID transceiver 18, 22 may also function as a data storage device. A visual display device or other input/output device may also be incorporated into the encoder 12 and the detector 16. In some embodiments portability and physical size objectives determine the amount of memory, data transfer rate, reusability, and other physical and cost characteristics.

Figure 3A:
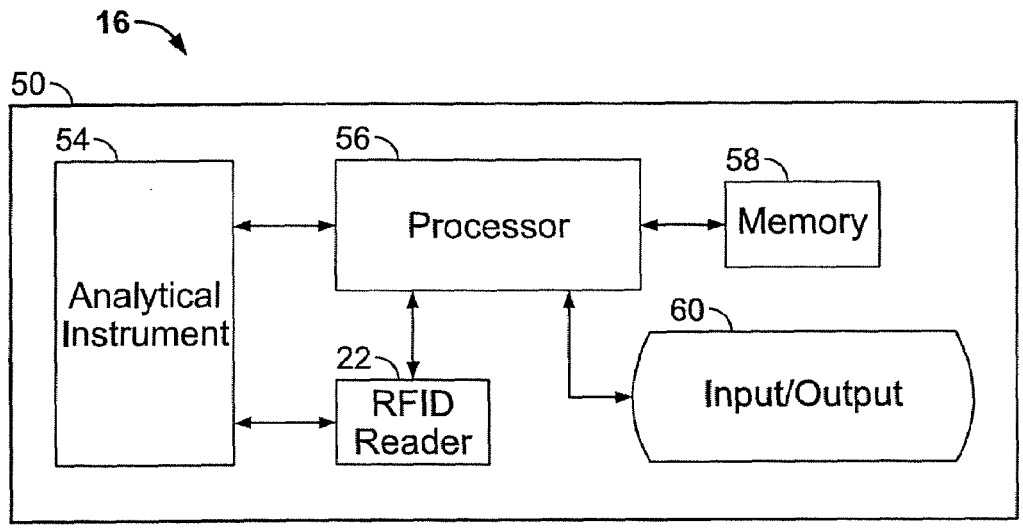
FIGS. 3A and 3B are block diagrams of embodiments of analytical detection devices suitable for reading a test cartridge such as that of FIG. 2.

The data transferred between the RFID device 20 and the analytical test instrumentation 24 can also be used to ensure the fidelity, and accuracy of the test. This may include, for example, test parameters and chain of custody data, test device expiration date, calibration levels, optimal test incubation time, serial number, batch information, test name, test type, etc. In some embodiments, test data is written to memory 58, 72 (see FIGS. 3A and 3B) in the detector 16 to maintain a record of test results.

In some embodiments, the information encoded into the RFID device 20 includes information which is used in controlling the conduct of the test such as controlling the performance of the test or the analysis of the results. Such data may include, but is not limited to, baseline correction data, calibration data, analytical instrumentation operating parameters, variable instrument control data, lot specific calibration information, and cutoff data for determining positive vs. negative result. Herein the term "controlling the conduct of the test" refers to performance of the test by an analytical test detector, for example detector 16 illustrated in FIGS. 1, 3A and 3B, wherein the detector based upon data from the RFID: 1) modifies the test parameters (e.g. time limit, test type selection reflectance cut off value), for performance of the test or analysis of the results; 2) modifies the course of the test or analysis (e.g. change the steps of analysis, etc.) and/or 3) modifies or adjusts the analytical instrumentation prior to or during the test, (e.g. adjusting instrument based on calibration data or test specification data). Thus, for example, the detector 16 could read the calibration data and then calibrate the detection instrumentation 24, and/or read the cutoff data and then use it to determine a positive or negative result. The test, in some embodiments, may also be aborted or flagged based upon other control information such as expiration data, authorization (e.g. authorized user, or authorized instrument) data, adulteration data, etc. In another embodiment, the detector may include a plurality of analytical test instruments 24 for different types of tests and the proper instrument for the detection and analysis is selected based upon test selection data preprogrammed into the RFID device 20.

In another embodiment, test specific information may preprogrammed onto a manufacturing batch of RFID devices that are subsequently incorporated into a production lot of discrete test devices at a later time during the manufacturing assembly process. Because stored information is retained by the RFID device and typically not altered during a manufacturing and device assembly process, unless pertinent manufacturing information for each discrete unit is desired, RFID devices may be pre-programmed prior to assembly or alternatively encoded following assembly as needed. The RFID devices may also be modified at some point or points during manufacturing as allowed by the manufacturing process and the capability of the RFID device, and thus information may be added, deleted or changed in multiple write events.

The RFID device 20 is some embodiments may use data encryption to securely limit access to information programmed or stored on the RFID device 20 of the cartridge 14, for example, to limit use to only authorized users and to provide a mechanism to ensure that the test has not been adulterated prior to testing. For example, in some embodiments, authorization passwords and/or authorized user access may be encrypted and stored on the RFID device 20 to limit use only to intended users and prevent unintended access by untrained, unauthorized or unintended users.

In some embodiments, the RFID device 20 is used to document critical processes of the test that may include completion of specific reagent, diluent and/or specimen additions and/or dates and/or times thereof and to prevent inadvertent omission of critical reagent additions or mismatch of specimens and/or reagents. In another alternative, use information may be written to a RFID device 20 associated with a single-use or disposable test device at the time it is first used, and once use has been documented by reading the RFID device 20, such information may be used to prevent accidental or purposeful re-use of the device.

Figure 2:
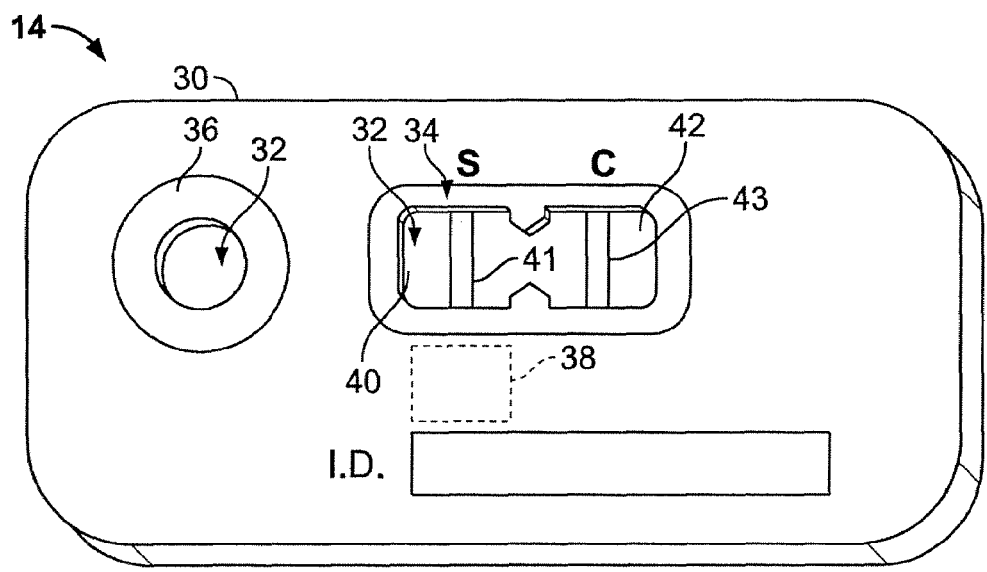
FIG. 2 is a schematic illustration of one embodiment of a lateral flow cartridge with an embedded RFID device.

Referring now to FIG. 2, there is shown a schematic illustration of one embodiment of a test device 14 (i.e. test cartridge 30 in the illustrated embodiment). The cartridge 30 may be constructed of any materials suitable for the intended test environment, for example, injection molded plastic. The illustrated embodiment of the cartridge 30 incorporates a conventional lateral flow test strip (e.g. an immunoassay test strip) as a test medium 32. The test medium 32 may be any suitable test medium. The example cartridge 30 illustrated is molded to include a slot 38 to accept a standard mini-RFID device such as manufactured by Hitachi Maxwell. Other known RFID devices may also be used. The illustrated example cartridge 30 has a sample application area (or port) 36, and a test window 34 having a visible test sample zone 40 and a visible control zone 42.

The cartridge 30 may be disposable and may, for example, incorporate wet or dry chemical and/or freeze dried biochemical components as part of the analytical test medium. Other test systems may also be used with the test cartridge 30. For example, the cartridge 30 may be a single-use, disposable and/or multi-use device and may comprise one or more tests and/or test methodologies including, but not limited to, lateral-flow immunoassays, embedded-flow immunoassays, clinical chemistry rapid tests, or general chemistry tests such as those for measuring pH or a specific protein. Examples of test measurement systems include, but are not limited to, a colorimetric, fluorimetric, chemiluminescent, electrochemiluminescent or other detectable indicator of test results that can be measured.

In one embodiment, the cartridge 30 may be a single use plastic cartridge housing with a molded two sided (upper and lower halves) locking design in which the two sides include the RFID device 20 and the test strip when it is assembled. The RFID device 20 is then protectively enclosed in the housing and located in a defined area 38 in the interior of the cartridge to enable accurate reading and writing to the device 20 by insuring proper alignment with the transceiver 22 in the detector 16.

In an exemplary lateral flow test, an amount of sample or specimen is added to the sample port, the test is allowed to run to completion via capillary action in accordance with known procedure. In this example, a positive result causes a color band 41 to appear in the sample window 40 which the test device (e.g. optical reader) can detect along with the control window color band 43. If negative, no color band appears in the sample window 40. The cartridge 30 is placed within the analytical test instrument (test device) 24 of the detector 16 for analysis and test results are generated by the analytical test instrumentation 24. In one embodiment, the test device 24 may be an optical reader which detects the color band in the sample window 40 enabling a colorimetric comparison to the color band in the control window 42.

The disclosed RFID analytical test system 10 may be used with a wide variety of analytical test processes. These tests may generate qualitative and/or qualitative results and include comparatively simplistic colorimetric diode source and detectors; optical, electromechanical, radiowave, electromagnetic and other physical measures of analytical properties. Other highly sophisticated analytical measurement systems may also be used that include, but are not limited to, nuclear magnetic resonance, calorimetric, enzymatic and fluorescent, particle-count and cell-count based analytical detection systems, etc. These systems may be hand-held, portable and/or operated within a fixed physical laboratory location. Testing may be performed in a variety of applications from field operations to large laboratory environments in a wide range of industries including, but not limited to medical, clinical, forensic, pharmaceutical, environmental, veterinary, biological, chemical, agricultural, waste management, hazardous chemical and drug testing.

The cartridge 20, in one example, may wholly-contain the RFID device 20 in a relatively precise, stable position which protects the RFID device 20 from the deleterious effects of physical environment and handling during use while maintaining the RFID device 20 unobtrusive to the conventional test process. This positioning of the RFID device 20 can be important because the maximum transmission distance between the transceiver 18, 22 and the RFID device 20 is limited by such features as the antenna and electronic characteristics of the RFID device 20. Other locations for the RFID 20 may also be used including attachment to the exterior of the cartridge.

The multiple read/write capability of the RFID device 20 enables use in single-use, disposable and multi-use analytical test systems. Multi-use (reusable) or multiple-test (single device with analytical capability to detect or quantitate more than one analyte on one test cartridge) devices may incorporate multiple RFID devices 20 in order to read or write test specific information for each test respectively. Specific placement of multiple RFID devices 20 within a fixed cartridge can enable specific information for each discrete test event to be written simultaneously, concomitantly or sequentially to and/or from each RFID device specific for each test event.

The detector 16 can utilize any RFID reader system. In one embodiment, illustrated in block diagram form in FIG. 3A, a conventional RFID reader (transceiver) 22 is incorporated within a table-top or portable housing 50 including a test instrument 54 such as an optical reader. The optical reader 54 measures the optical reflectance of the calorimetric band 41, 43 that appears on the test strip as shown in the illustrated example of FIG. 2. The detector 16 of FIG. 3A also may include a processor 56 to provide control and processing and associated memory 58 coupled thereto for storage. Input/output devices 60, such as a keypad and visual display, are coupled to the processor 56, as shown, for user input of data and display of results and other information. In the example shown, the analytical instrumentation 54 is coupled to the processor 54 and the transceiver 22 to permit control of the instrument 54 as well as exchange of data between the instrument 54, the processor 56 and the transceiver 22.

Figure 3B:
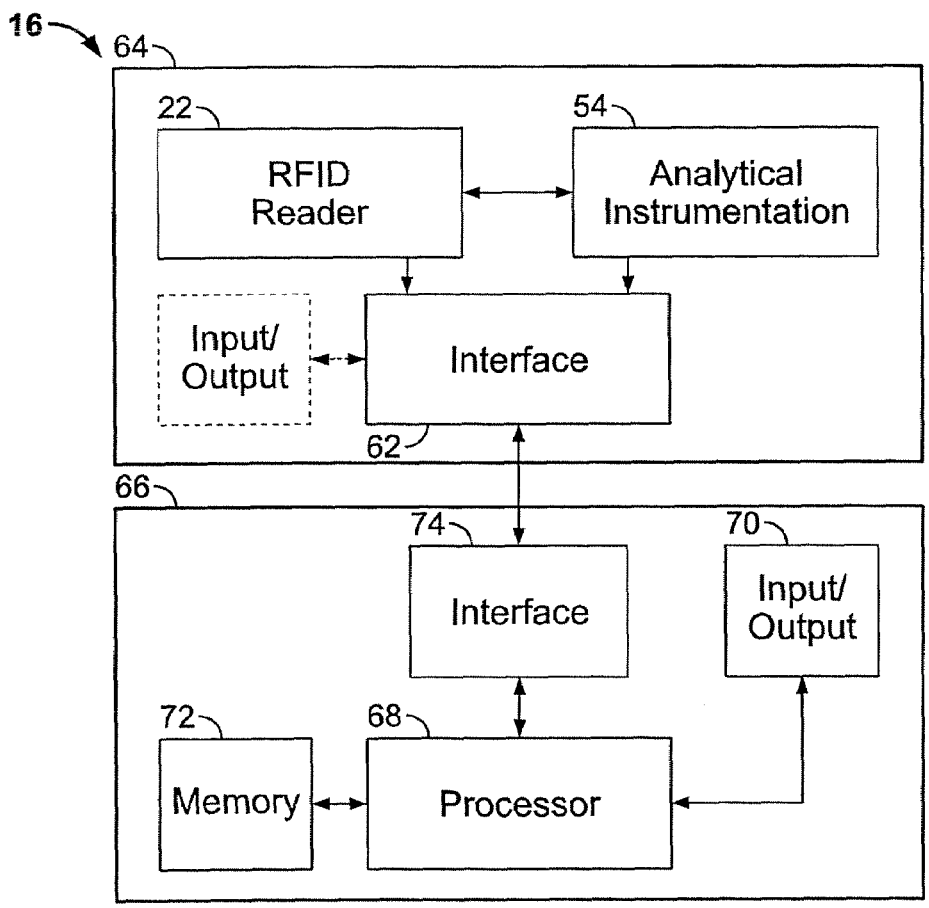

In another embodiment illustrated in block diagram form in FIG. 3B is a detector 16 including a transceiver/reader 22, coupled to analytical instrumentation 54 and conventional interface circuitry 62 in an attachable or wireless reader system 64. The system 64 may be used in conjunction with another digital device 66 such as a Personal Digital Assistance (PDA), which includes a processor 68, a user interface Input/Output 70 (e.g. visual display, keys, etc.), conventional interface circuitry 74 and memory 72 coupled together as shown. The interface circuitry 62, 70 may be any known type of interface including, for example, wired or wireless interfaces. Thus, for example, conventional PDA 68 may be combined with the attachable reader system 64 which communicate through the interface circuits 62, 74 to control the test performance and analysis, and generate and communicate test results. Programming for the processor 56, 66 permits control of all aspects of the two-way RFID data transfer during the test event.

Figure 4:
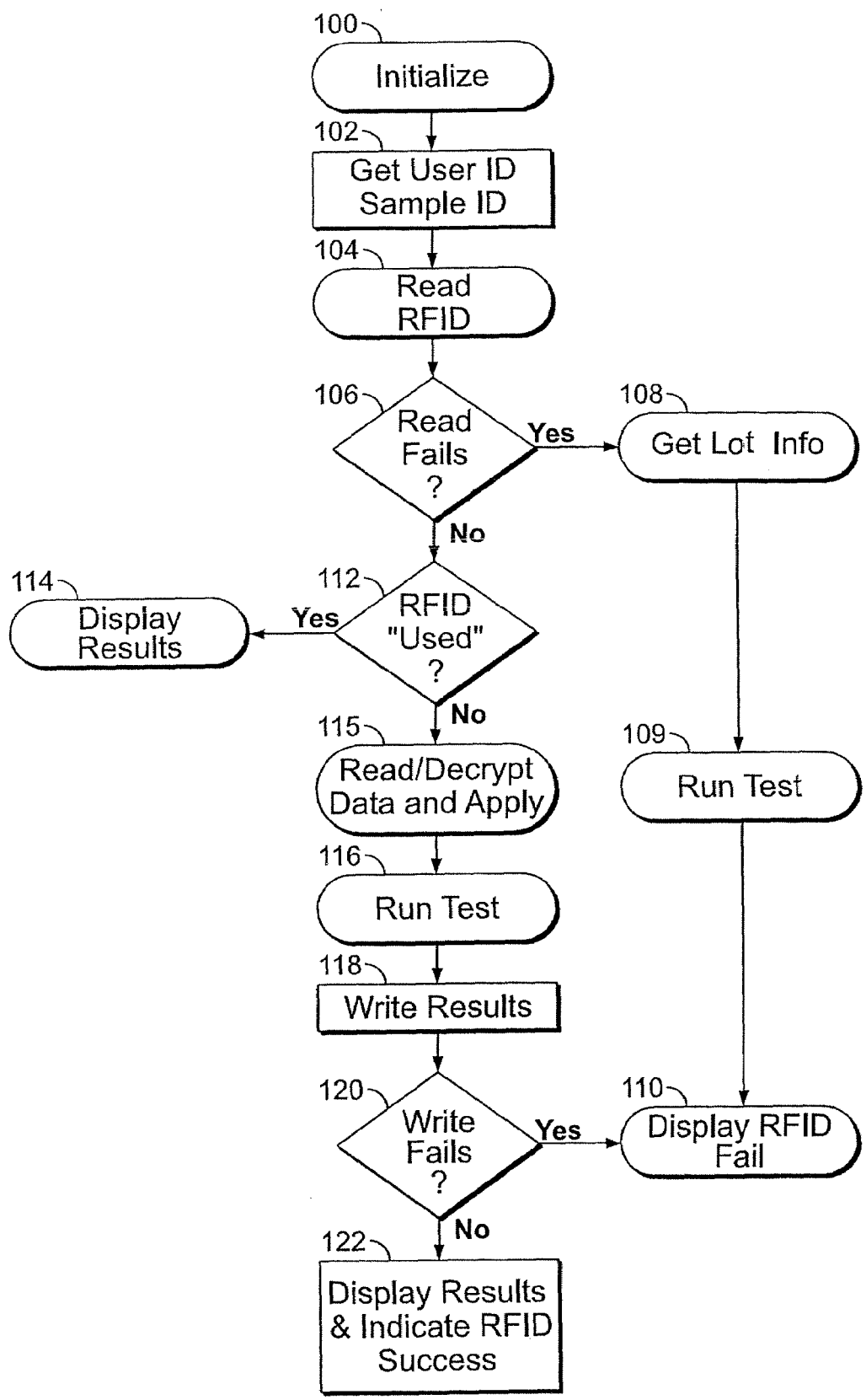
FIG. 4 is a flow chart of one embodiment of decision flow for an analytical detection device such as those of FIG. 3A and FIG. 3B.

Upon completion of a test (e.g. after the test incubation period for the lateral flow immunoassay test), the test cartridge 14 is analyzed using the detector 16 to determine the test results. FIG. 4 illustrates a flow chart of one embodiment of the analysis process of the detector 16 wherein the system is first initialized, and user and sample ID's are entered by the user, for example, through the input/output 60, 70 as illustrated at steps 100, and 102. The RFID device 20 is then read (see step 104) to obtain such preprogrammed cartridge batch information as test type (anthrax, plague, etc.), manufacturing lot number, identification and/or unit production number, raw material batch numbers, manufacturing date and time, test expiration data, tracking number and other manufacturing information to ensure proper use of the test. Additional information which may be pre-programmed into the RFID device 20, in some embodiments, includes, but is not limited to, calibration data, lot-specific analytical information such as baseline correction, absorbance cut-off for determination of positive/negative results, and encrypted information from the manufacturer to ensure the test has not been altered and to prevent unauthorized use.

Encryption may also be used for any or all of the data stored on the RFID device 20. If encryption is used, a decryption step also is performed at or after the RFID device is read. Post read encryption may also be employed to encrypt the test results before writing them to the RFID device 20 or detector 16.

If the analytical instrument fails to read the test cartridge 14, the user may be asked to enter missing information (e.g. lot information), thereby allowing the test to be run manually, and an indication of the read failure or absence of RFID is displayed as shown at steps 106, 108, 109 and 110. If the read is successful, the data is checked to determine if the cartridge was previously used, and if so, the results are displayed as shown at steps 102 and 114. In addition, in some embodiments, data may be decrypted as shown at step 115 (if encrypted), and/or data for verification of the authenticity of the test device or for other requirements such as expiration is read. This data is then used to determine if the test shall proceed or not, and/or be flagged, if appropriate. In addition, data regarding control of the test such as calibration data, cutoff data, and baseline data may be retrieved at step 115 and used in performing the test or as part of the test analysis.

If the RFID data shows the test cartridge has not previously been used, the test results are determined and analyzed at step 116. The results, which may include an error result or abort by the user, are then written to the RFID device 20 and/or to the memory 55, 72 of the detector 16 at step 118. Some or all of this data may be encrypted in some embodiments before being written. The write process is tested by the detector 16 to determine if it was successful, and if not the results are displayed with an RFID failure indication as illustrated at steps 120 and 110. If successful, the results are displayed and flagged with an indication of a successful RFID write as shown at step 122.

The test results may include, but are not limited to, sample value, raw analytical results, and interpreted test results including indication of abnormal high or low results notification, error-in-processing information including failed analysis because of analytical system malfunctions, test results out of range, other irregularities, date and time that the test was performed, system operator, quality control information, reader serial number, test mode and any pertinent service and maintenance information. The RFID data in some embodiment is encrypted and in some embodiments may be in Write Once Only format. These features can be used to increase security and ensure chain of custody.

While calibration and control information have been illustrated in some examples as incorporating into a standard passive RFID device, it should be apparent that extension to active RFID devices and more complex RFID systems are equally applicable. Similarly, for example, the RFID device type, size and placement including, but not limited to, the location of the RFID device either on or embedded in the test device; read/write options to transfer information from or to a single or reusable test system, the analytical reader or a data management system; the location of use in field, mobile and/or permanent laboratory settings; use of the RFID device for control, monitoring, and for restricting access to intended users; data recording or information transfer to an analytical test system and subsequent data management; etc. can all vary.

Specific embodiments of systems and apparatus for analytical testing with radio frequency identification has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

What is claimed is:

1. An automated clinical test system comprising:
   a) a test cartridge for use in conducting automated clinical testing including a test medium and an RFID device preprogrammed with information relating to the test including data for modifying the performance of the test during the test;
   b) an analytical detection device including an RFID transceiver adapted to transfer data to and from the RFID device and coupled to test detection instrumentation adapted to analyze the test medium responsive to the information relating to the test using a multiple step analytical test, and adapted to modify or adjust the performance of the test during the test based upon the preprogrammed information in the RFID device.

2. The test system of claim 1 wherein a plurality of RFID devices are incorporated in the test cartridge to enable incorporation of multiple tests on the cartridge and enable writing of results of different tests to a different RFID device.

3. The test system of claim 1 wherein the RFID device includes preprogrammed service and maintenance information.

4. The test system of claim 1 wherein the test cartridge includes test selection data to permit selection of one of a plurality of tests to be performed on the test cartridge.

5. The test system of claim 1 wherein the information related to the test includes at least calibration information.

6. The test system of claim 1 wherein the test is flagged based upon expiration data.

7. The test system of claim 1 wherein at least some encrypted test result data is programmed on to the RFID device.

8. The test system of claim 1 wherein the information relating to the test is variable instrument control data.

9. The test system of claim 1 wherein the RFID device is adapted to receive and store data to document completion of critical processes of the test.

10. A method for conducting an analytical test using an analytical instrument comprising:
- exposing a test medium to a sample to be tested, the test medium having an RFID device associated therewith;
- reading data for controlling conduct of test analysis of the test medium from the RFID device;
- controlling the conduct of the test based upon the data by at least one of changing at least one step of the test analysis, and adjusting or modifying the analytical instrument during the test; and
- writing the results of the test onto the RFID device.

11. The method of claim 10 further comprising flagging the test based upon expiration data.

12. The method of claim 10 wherein the step of controlling comprises at least one of: re-calibrating before testing using calibration data from the RFID device, and determining test results based upon baseline correction data from the RFID.

13. The method of claim 10 further comprising programming encrypted test result data into the RFID device.

14. The method of claim 10 further comprising preprogramming baseline correction data into the RFID device and performing a baseline correction of the test.

* * * * *